United States Patent
Liu et al.

(10) Patent No.: US 9,044,327 B2
(45) Date of Patent: Jun. 2, 2015

(54) STRUCTURE IMPROVEMENT OF AN ORTHOPAEDIC IMPLANT OF AN ARTIFICIAL KNEE JOINT

(71) Applicant: UNITED ORTHOPEDIC CORP., Hsinchu (TW)

(72) Inventors: Yu-Liang Liu, Hsinchu (TW); Cheng-Kuang Lu, Hsinchu (TW); Jiann-Jong Liau, Hsinchu (TW)

(73) Assignee: UNITED ORTHOPEDIC CORP., Hsinchu (TW)

( * ) Notice: Subject to any disclaimer, the term of this patent is extended or adjusted under 35 U.S.C. 154(b) by 33 days.

(21) Appl. No.: 13/940,531

(22) Filed: Jul. 12, 2013

(65) Prior Publication Data

US 2013/0304222 A1    Nov. 14, 2013

Related U.S. Application Data

(63) Continuation-in-part of application No. 12/591,435, filed on Nov. 19, 2009, now abandoned.

(51) Int. Cl.
*A61F 2/38* (2006.01)
(52) U.S. Cl.
CPC ............. *A61F 2/3868* (2013.01); *A61F 2/3886* (2013.01); *A61F 2/389* (2013.01)
(58) Field of Classification Search
CPC .................. A61F 2/3868; A61F 2/389; A61F 2002/3079; A61F 2002/30774; A61F 2002/305; A61F 2002/30604; A61F 2002/3036; A61F 2002/30433; A61F 2002/30436; A61F 2002/30476; A61F 2002/30332
USPC ........... 623/20.15, 20.27, 20.28, 20.32–20.34
See application file for complete search history.

(56) References Cited

U.S. PATENT DOCUMENTS

| | | | | |
|---|---|---|---|---|
| 6,004,352 | A | * | 12/1999 | Buni ........................... 623/20.33 |
| 2005/0203631 | A1 | * | 9/2005 | Daniels et al. ............. 623/20.32 |
| 2009/0088861 | A1 | * | 4/2009 | Tuke et al. ................. 623/20.32 |

* cited by examiner

*Primary Examiner* — Randy Shay
(74) *Attorney, Agent, or Firm* — Bacon & Thomas, PLLC

(57) ABSTRACT

A structure improvement of orthopaedic implant for connecting a distal femur and a proximal tibia, and a stem was implanted into the proximal tibia, in which formed to allow inter-engagement between the stem of the tibia and the structure improvement of orthopaedic implant. The structure improvement of orthopaedic implant includes a tibial baseplate, a tibial insert, and a reinforcement. The tibial baseplate forms a recess having a bottom that has a central portion defining a through hole extending through the tibial baseplate. The tibial insert includes a support, a through region, and a projection, wherein an end of the tibial insert forming the projection corresponding to the recess of the tibial baseplate for press-fitting to the tibial baseplate. The reinforcement is inset in the tibial insert and includes a sleeve and a bolt. As such, the advantages of stable coupling includes force resistance, avoids insert loosening then extends prosthetic longevity.

2 Claims, 7 Drawing Sheets

STRUCTURE IMPROVEMENT OF AN ORTHOPAEDIC IMPLANT OF AN ARTIFICIAL KNEE JOINT

FIELD OF THE INVENTION

The present invention relates to a structure improvement of an orthopaedic implant of a knee joint, and in particular to an orthopaedic implant of an artificial knee comprising a special design of a reinforcement to enhance stable coupling between a poly tibial insert and a metal tibial baseplate to offer the advantages of the resistance against external forces, the prevention of the deformation, and the extension of the lifespan, and to be applicable to severe bone damage or revision knee surgery.

BACKGROUND OF THE INVENTION

Due to aging, joints of human beings may suffer wear or degradation caused by long term use or degeneration, leading to pain or incapability of providing proper moving functions, as a consequence of which daily living is affected. When a joint suffers severe pathological changes, artificial knee joint replacement provides a measure to release the pain and improve joint function. The artificial knee joint is often composed of components made of metal or plastics and can be fixed to bones to replace the original knee joint to restore the normal function of the knee joint.

Total knee arthroplasy (TKR) is a common surgical procedure to treat degradation or lesion of knee joint. A typical artificial knee joint comprises a femoral component, a tibial baseplate, a tibial insert, and a patellar component. The tibial baseplate is fixed to a tibial surface, and the tibial insert is coupled to the tibial baseplate through mechanical locking mechanism. The stability of the knee joint heavily depends on the constrained design between femoral component and tibial insert which was locked with tibial baseplate. Therefore, how to secure locking strength between the tibial insert and the tibial baseplate was one of most important issue to achieve successful TKR. The tibial insert forms thereon a support that constrains the movement between the femoral implant and the tibial insert, but it is often made of plastics and is susceptible to fracture caused by long resistance against external forces acting thereon. Daily activity of human beings causes loads and shear forces acting on the artificial knee joint, especially the tibial insert post and this may cause dislocation between the tibial insert and the tibial baseplate, or may even separate the tibial insert from the tibial baseplate. Thus, the support formed on the tibial insert must be of sufficient mechanical strength and proper coupling between the tibial insert and the tibial baseplate is important and necessary.

An L-shaped reinforcement inset in the tibial insert is a common way to improve the mechanical strength of the support formed on the tibial insert. Since a metal object is inset in the support of the tibial insert, the mechanical strength of the support for resistance against external forces is increased. However, this arrangement only improves the stability between the tibial insert and the femoral implant. One common way for coupling the tibial insert and the tibial baseplate is using a bolt to joint the two components. This only improves the coupling between the two components, but does not increase the capability of resisting shear force. Further, the bolt and the tibial insert are separate parts, which are combined together only when they are put into use. This lowers the efficiency of operation.

Thus, a good design of artificial knee joint must offer: (1) sufficient stability for movement of the knee joint for reducing unnecessary activity or dislocation of joint, (2) sufficient strength for resisting external forces, (3) protection against excessive wear of implants for extension of lifespan of the implants, and (4) improved operation efficiency for reducing the time required for surgical operations.

In view of the above drawbacks, the present invention aims to provide a novel design of orthopaedic implant that overcomes the above problems.

SUMMARY OF THE INVENTION

An objective of the present invention is to provide a structure improvement of an orthopaedic implant, which comprises a reinforcement inset in a tibial insert and coupled, in a downward direction, to a stem adaptor to drive a sleeve of the reinforcement to project beyond a bottom of the tibial insert for fitting into a groove defined in a tibial baseplate to provide the efficacies of stable coupling, resistance against external forces, the prevention of the deformation, and the extension of the lifespan thereby enhancing practicability and inventiveness of the present invention.

Another objective of the present invention is to provide a structure improvement of the orthopaedic implant, wherein a reinforcement is directly set inside an accommodating hole of a through region defined in a tibial insert and a sleeve of the reinforcement has a circumferential outer surface that forms threading or is made roughened, thereby providing the efficacies of increasing operation efficiency, providing safety of use, and making a stable coupling and thus enhancing the inventiveness and safety of the present invention.

A further objective of the present invention is to provide a structure improvement of the orthopaedic implant, wherein the components of the orthopaedic implant are of modular designs and suit for difference of individuals and allow for partial replacement to thereby offer the efficacies of being easy to use and reducing costs and thus enhancing the practicability and convenience of the present invention.

To achieve the above objectives, the present invention provides a structure improvement of the orthopaedic implant for connecting a distal femur and a proximal tibia, and a stem was implanted into proximal tibia, wherein an end of the stem formed a coupling hole with inner thread, in which formed to allow inter-engagement between the stem of the tibia and the structure improvement of the orthopaedic implant. The structure improvement of the orthopaedic implant comprises a tibial baseplate, a tibial insert, and a reinforcement. The tibial baseplate forms a recess having a bottom that has a central portion defining a through hole extending through the tibial baseplate, and an end of the stem is inserted in the through hole, and the through hole has a top circumference that defines a circumferential groove extending outward. The recess has a side wall defining a retention slot. The tibial insert includes a support and a projection, wherein an end of the tibial insert forming the projection corresponding to the recess of the tibial baseplate for press-fitting to the tibial baseplate. A retention pawl is formed on one side of the projection and is engageable with the retention slot of the tibial baseplate. A support is formed on the opposite end of the tibial insert and forms a through region that extends through the tibial insert, wherein the through region includes a bore and an accommodating hole, wherein the accommodating hole disposed close to the bore, and the diameter of the accommodating hole is greater than the diameter of the bore. The tibial insert forms two curved surfaces on opposite sides of the support to support contact and rolling. The reinforcement is fit in the accommodating hole and comprises a sleeve and a bolt, wherein an end of the sleeve forms a first opening, and the opposite end of the sleeve forms a stop with a second opening, wherein the first opening communicates with the second opening, and the bolt is movable received in the sleeve, wherein the bolt comprises a bolt head and a bolt body, and the diameter of the bolt head is greater than the diameter of the second opening and the diameter of the bore, and the diameter of the bolt body is smaller than the diameter of the second opening, and the bolt body is threading engagement with the inner thread of the coupling hole of the stem to drive the sleeve of the reinforcement to project beyond an end of the tibial insert for fitting into the groove of the tibial baseplate. As such, the advantages of stable coupling, resistance against stress, the prevention of the deformation, the extension of the lifespan, increasing safety of use are provided so as to realize practicability, inventiveness, safety, and convenience.

BRIEF DESCRIPTION OF THE DRAWINGS

The present invention will be apparent to those skilled in the art by reading the following description of a preferred embodiment thereof with reference to the drawings, in which.

DETAILED DESCRIPTION OF THE PREFERRED EMBODIMENT

Figure 1:
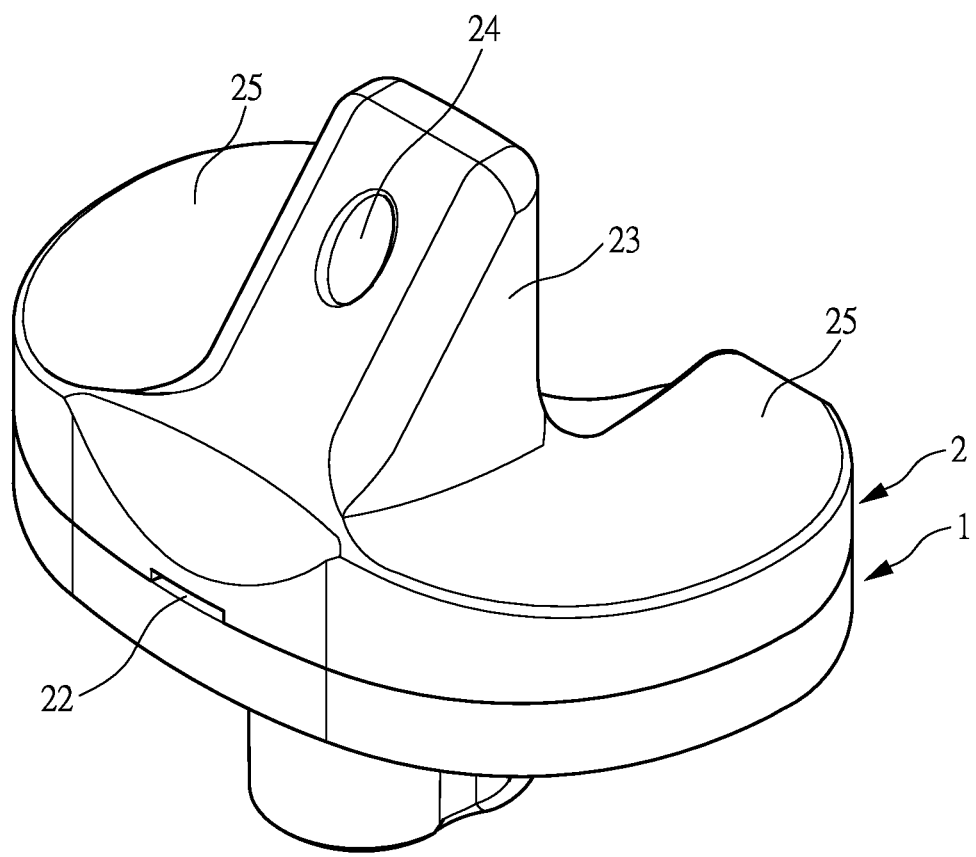
FIG. 1 a perspective view of an orthopaedic implant constructed in accordance with the present invention.
Figure 2:
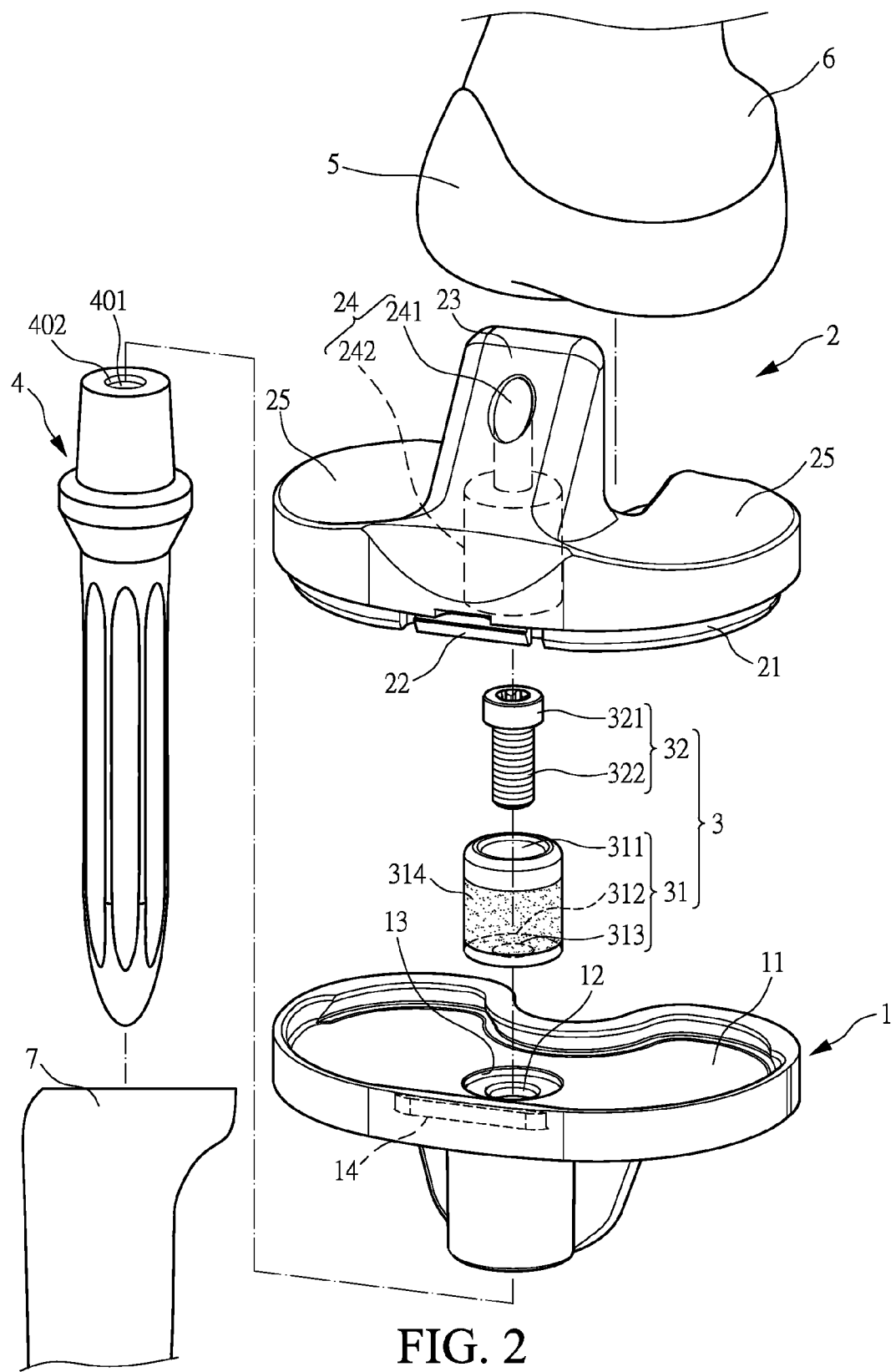
FIG. 2 an exploded view of the orthopaedic implant constructed in accordance with the present invention.
Figure 3:
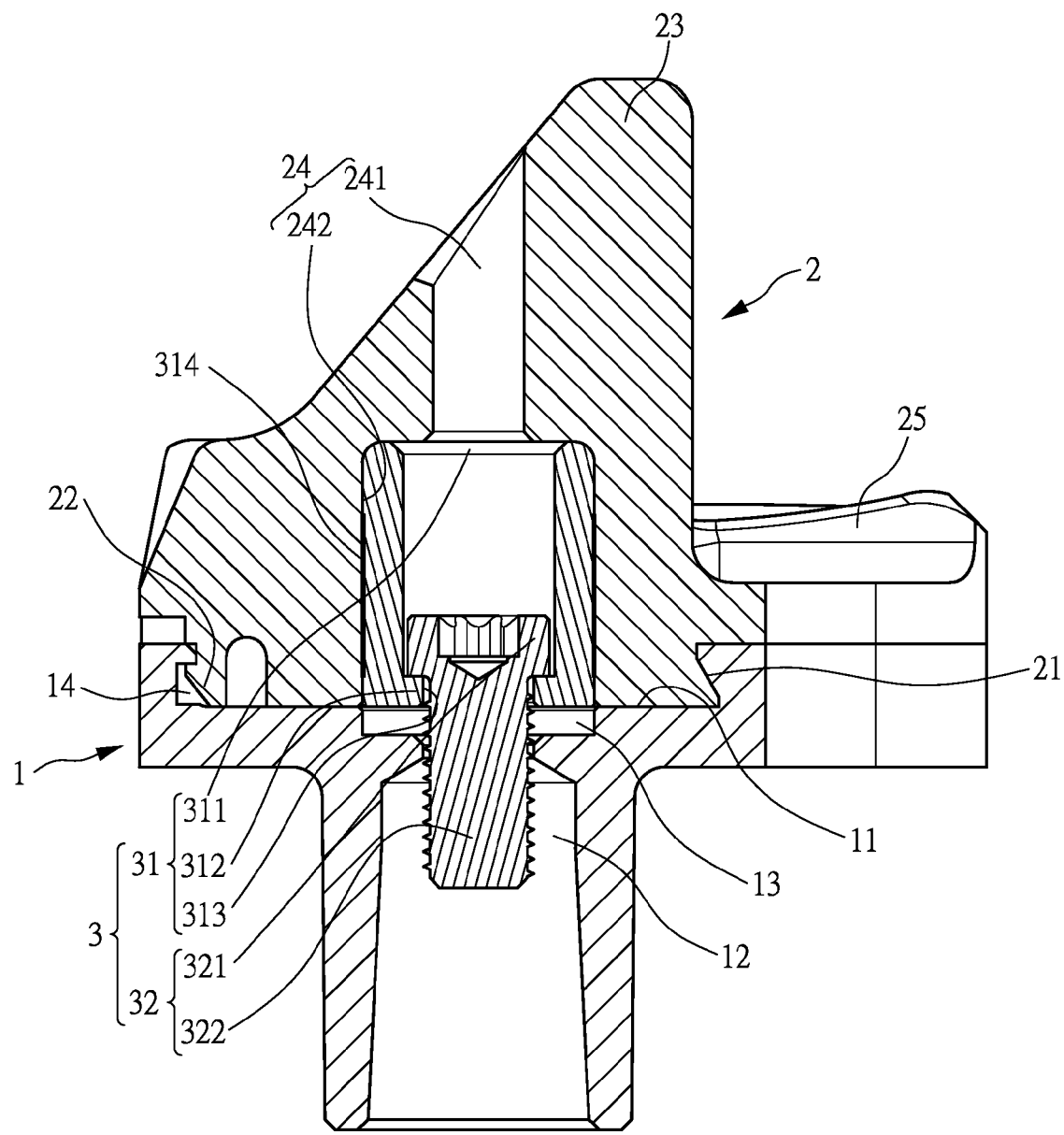
FIG. 3 a cross-sectional view of the orthopaedic implant constructed in accordance with the present invention.

With reference to the drawings and in particular to FIGS. 1-3, which show, respectively, a perspective view, an exploded view, and a cross-sectional view of an orthopaedic implant constructed in accordance with the present invention, the orthopaedic implant of the present invention connected a femur 6 and a tibia 7, and a stem 4 was implanted into the tibia 7, wherein an end of the stem 4 formed a coupling hole 401 with inner thread 402, in which formed to allow inter-engagement between the stem 4 of the tibia 7. The orthopaedic implant of the present invention comprises a tibial baseplate 1, a tibial insert 2, and a reinforcement 3. The orthopaedic implant of the present invention comprises a tibial baseplate 1, a tibial insert 2, and a reinforcement 3.

The tibial baseplate 1 is of a modular design having various sizes and forms a recess 11. The recess 11 has a bottom that has a central portion defining a through hole 12 extending through the tibial baseplate, and an end of the stem 4 is inserted in the through hole 12 (see FIG. 6), and the through hole 12 has a top circumference that defines a circumferential groove 13 extending outward, and the recess 11 has a side wall defining a retention slot 14 for retaining engagement, and the through hole 12 and the stem 4 have ends that are of inclination according to Morse taper connection.

The tibial insert 2 is of a modular design of various sizes and includes a projection 21, a support 23, and a through region 24, wherein an end of the tibial insert 2 forms the projection 21 corresponding to the recess 11 of the tibial baseplate 1 for coupling to, such as press-fitting, the tibial baseplate 1. (In the embodiment illustrated, the side wall of the recess 11 of the tibial baseplate 1 is made in the form of a dovetail and consequently, a side surface of the projection 21 is also made dovetailed.) A retention pawl 22 is formed on one side of the projection 21 and the retention pawl 22 is engageable with the retention slot 14 of the tibial baseplate 1. A support 23 is formed on the opposite end of the tibial insert 2, substantially at a central portion thereof, for extending into a femoral implant 5 (see FIG. 6) to provide relative movement of the femoral implant 5 on the tibial insert 2. The support 23 forms a through region 24 that extends through the tibial insert 2, wherein the through region 24 includes a bore 241 and a accommodating hole 242, wherein the accommodating hole 242 disposed close to the bore 241, and the diameter of the accommodating hole 242 is greater than the diameter of bore 241, and the tibial insert 2 forming two curved surfaces 25 on opposite sides of the support 23 to support contact and rolling of the femural implant 5 thereon. (The two curved surfaces 25 are smooth arc surfaces for reducing stress concentration and wear of the tibial insert 2.)

Figure 7:
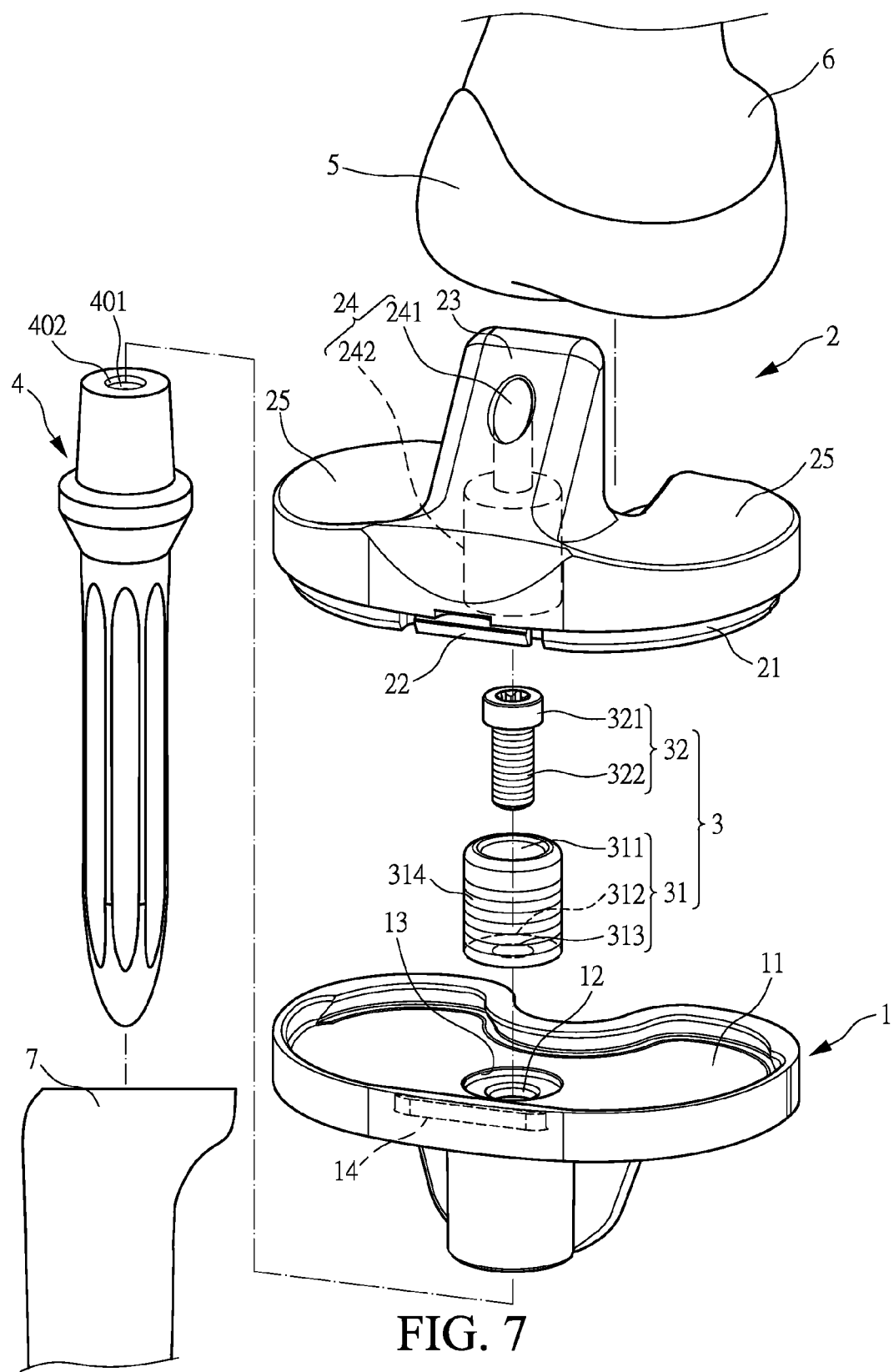
FIG. 7 is an exploded view of the orthopaedic implant constructed in accordance with the present invention having the reinforcement having a threaded outer circumferential surface.

The reinforcement 3 is fit in the accommodating hole 242 and comprises a sleeve 31 (In the embodiment illustrated, the sleeve 31 has an outer circumferential surface 314 that is provided with thread (see FIG. 7) or is made roughened (see FIG. 2) to facilitate tight engagement between the sleeve 31 and the tibial insert 2) and a bolt 32, wherein an end of the sleeve 31 forms a first opening 311, and the opposite end of the sleeve 31 forms a stop 312 with a second opening 313, in which the first opening 311 communicates with the second opening 313, and the bolt 32 is movable received in the sleeve 31. The bolt 32 comprises a bolt head 321 and a bolt body 322, and the diameter of the bolt head 321 is greater than the diameter of the second opening 313 and the diameter of the bore 241, and the diameter of the bolt body 322 is smaller than the diameter of the second opening 313, and the bolt body 322 is threading engagement with the inner thread 402 of the coupling hole 401 of the stem 4 to drive the sleeve 31 of the reinforcement 3 to project beyond an end of the tibial insert 2 for fitting into the groove 13 of the tibial baseplate 1. When the bolt 32 breaks or loosens, the bolt 32 is not allowed to get out of the tibial insert 2 to cause damage or infection to the patient.

Figure 4:
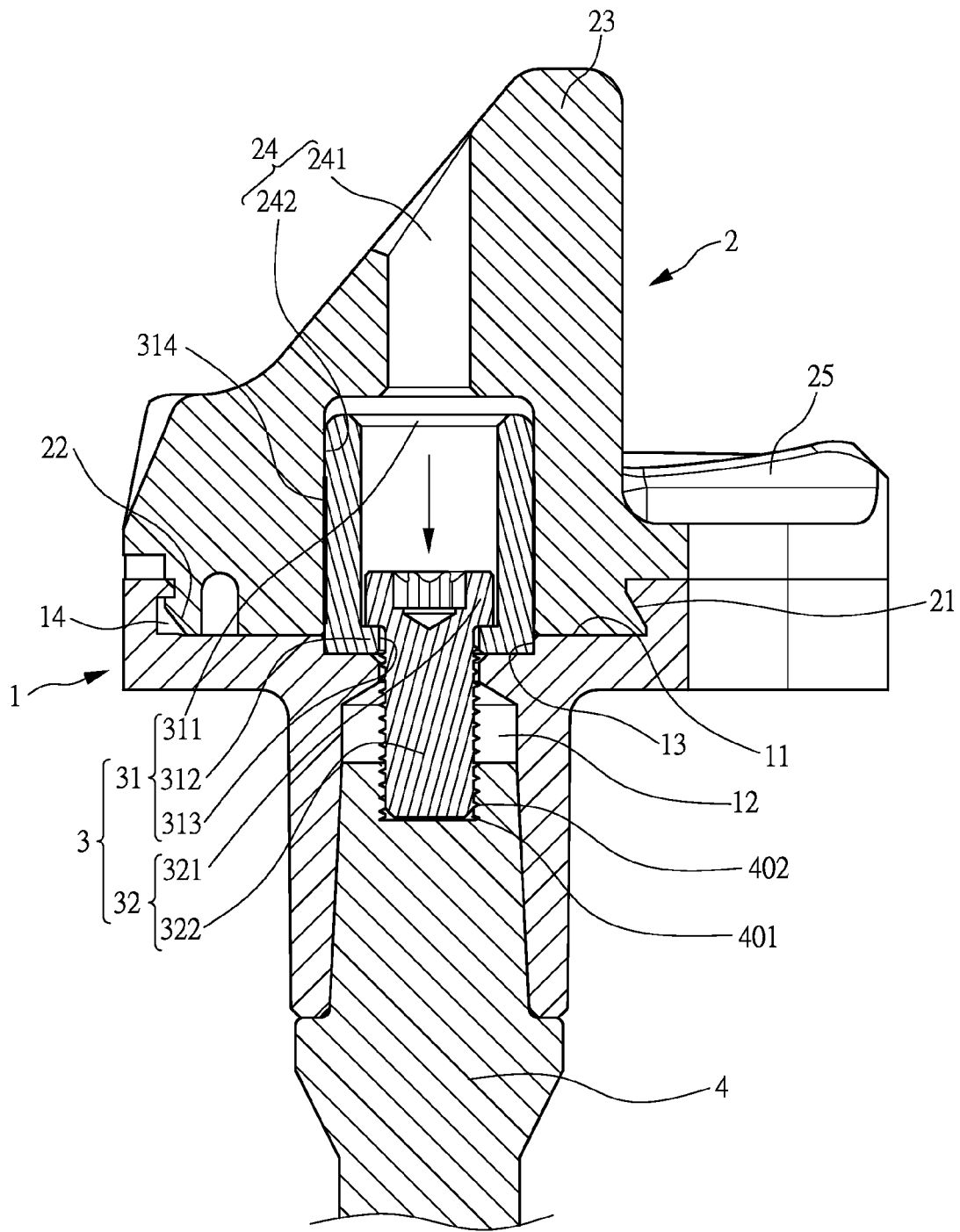
FIG. 4 a cross-sectional view of the orthopaedic implant constructed in accordance with the present invention.
Figure 5:
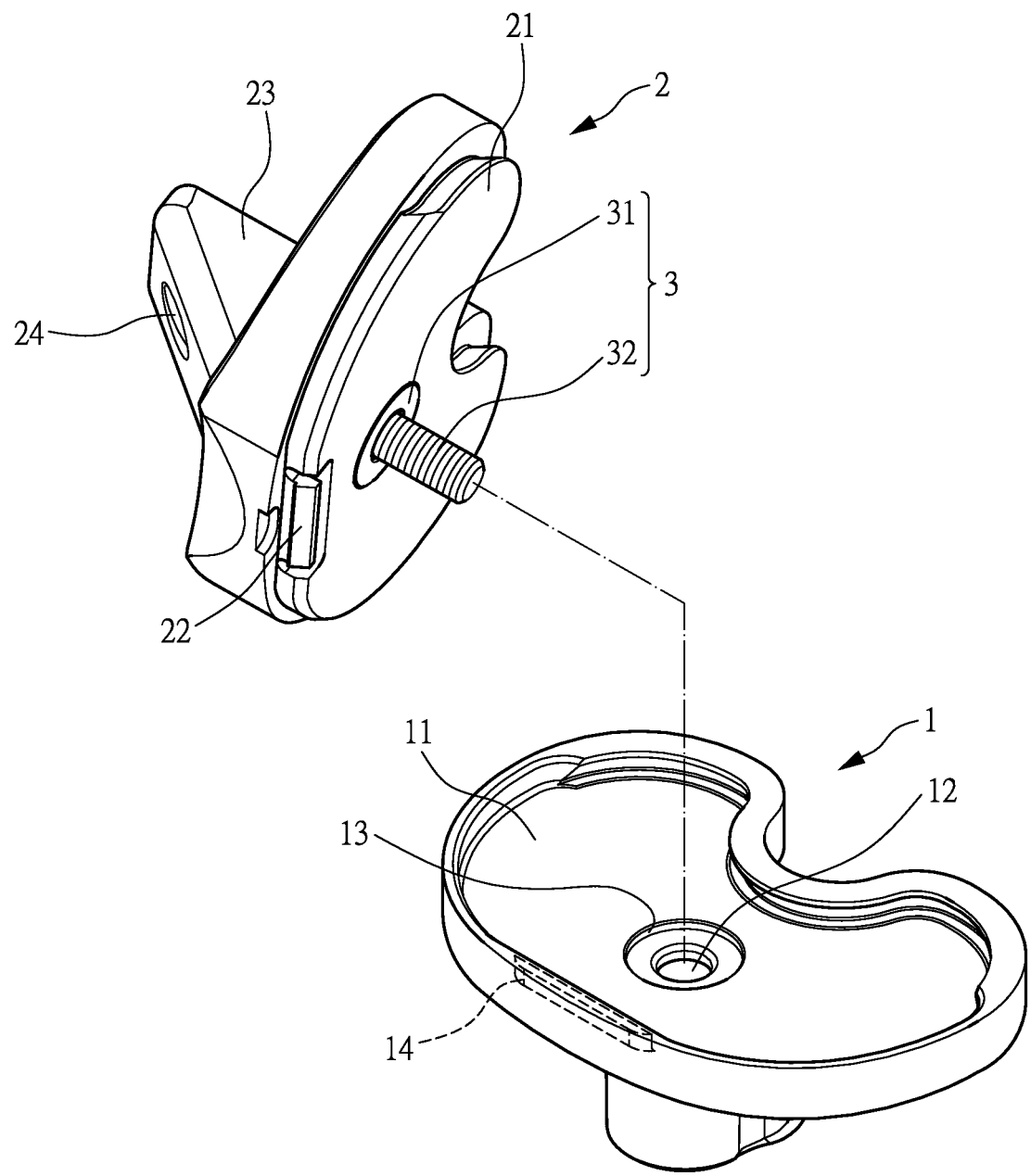
FIG. 5 is a schematic view showing an assembled form of the orthopaedic implant of the present invention.
Figure 6:
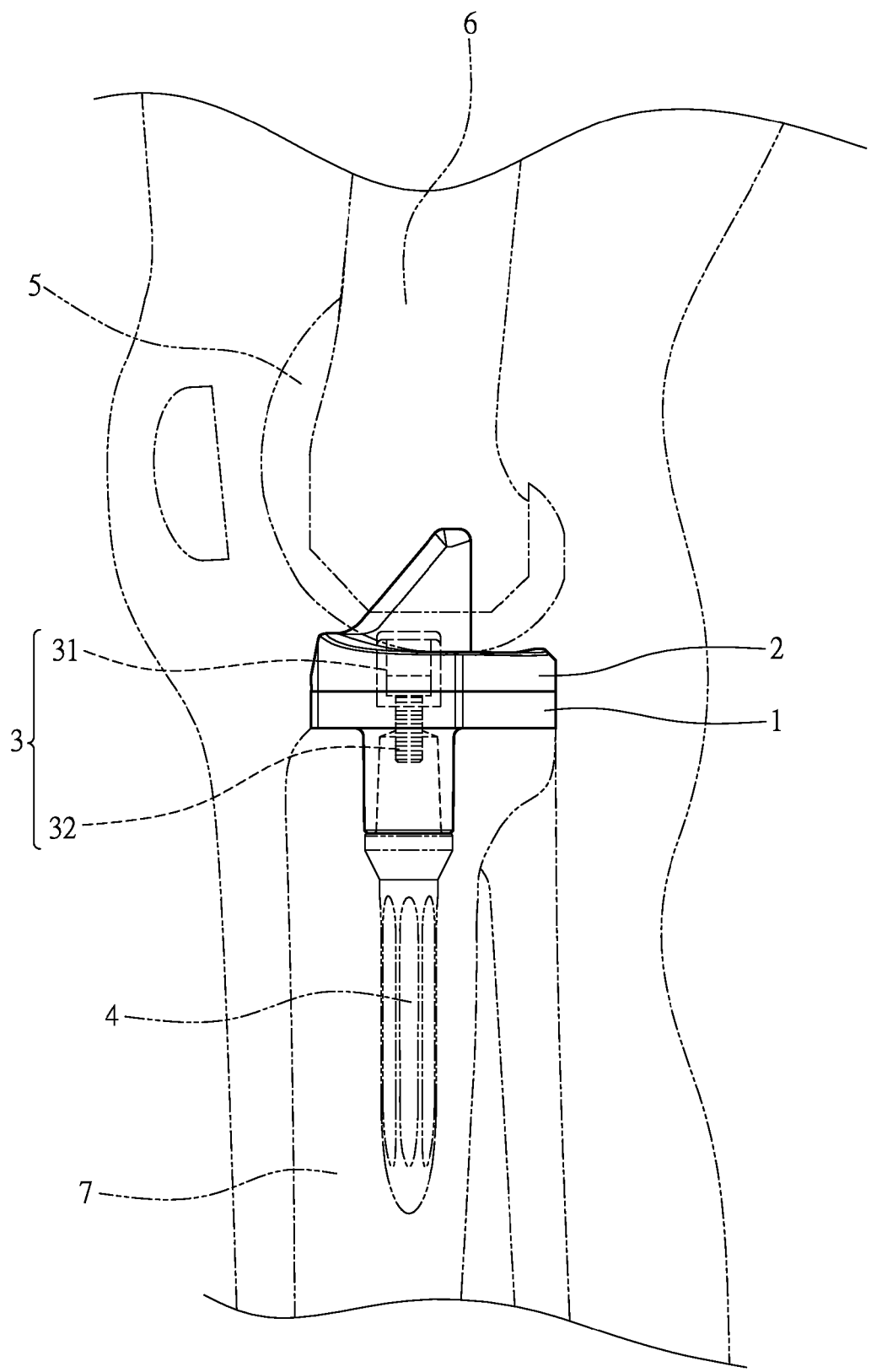
FIG. 6 is a schematic view showing a use of the orthopaedic implant of the present invention.

With reference to the drawings and in particular to FIGS. 4-6, which show, respectively, a cross-sectional view and two schematic view of an orthopaedic implant constructed in accordance with the present invention. Referring to FIGS. 4 and 6, which are schematic views respectively showing an assembled form of the present invention and the use of the present invention, in use, the tibial insert 2 is press-fit to the tibial baseplate 1. (In the embodiment illustrated (see FIG. 5), after the formation of the tibial insert 2, the reinforcement 3 is already inset in the tibial insert 2.) Since the projection 21 of the tibial insert 2 is formed to correspond to the recess 11 of the tibial baseplate 1, they can be tightly and efficiently coupled to each other and with the retention pawl 22 on one side of the tibial insert 2 engaging the retention slot 14 of the tibial baseplate 1, a more secured and more stable coupling between the tibial insert 2 and the tibial baseplate 1 can be realized to prevent undesired separation and to improve safety of use. Further, the lower portion of the through hole 12 of the tibial baseplate 1 is coupled to the stem 4 and the inclination of the through hole 12 and the stem 4 is set in the form of Morse Taper connection, so that easy mounting and dismounting can be realized there between. An end of the stem 4 forms a coupling hole 401 (see FIG. 4) inside which inner thread 402 is formed to allow inter-engagement between the coupling hole 401 and the bolt 32 of the reinforcement 3. A tool, such as a screwdriver, may be inserted into the sleeve 31 that is fit in the accommodating hole 242 of the tibial insert 2 to rotate the bolt 32 relative to the stem 4 and at the same time also drive the sleeve 31 to project beyond an end of the tibial insert 2 to fit into the groove 13 of the tibial baseplate 1 (see FIG. 4) for improving resistance against shear force after they are coupled. Further, the support 23 that is formed on the central portion of the top of the tibial insert 2 is inserted into the femoral implant 5 to provide contact and rolling of the femoral implant 5 on the curved surfaces 25 of the tibial insert 2. Since the curved surfaces 25 of the tibial insert 2 are smooth arc surfaces, when the femoral implant 5 rolls on the curved surfaces 25 of the tibial insert 2, the knee joint is allowed to undergo smooth bending and stretching movements with reduced stress concentration and wear of the tibial insert 2. The reinforcement 3 of the present invention that is inset in the tibial insert 2 helps reinforcing the tibial insert 2 to resist stress induced in the tibial insert 2 by the movement of the femoral implant 5 thereby realizing protection against damage and deformation caused thereby and extension of the service life. Further, the bolt 32 of the reinforcement 3 is coupled to the stem 4 to make the sleeve 31 fit into the groove 13 for improving resistance against shear force. Further, due to the unique configuration of the through region 24, when the bolt 32 of the reinforcement 3 breaks or loosens, the bolt 32 is not allowed to get out of the tibial insert 2 to cause damage or infection and also offering safety of use. In addition, the arrangement that sets the reinforcement 3 inside the tibial insert 2 helps improving efficiency of operation.

The present invention provides an orthopaedic implant that has the following advantages. A reinforcement 3 is inset in a tibial insert 2 and the reinforcement 3 comprises a bolt 32 that is coupled, in a downward direction, with a stem 4, so as to allow a sleeve 31 of the reinforcement 3 to project beyond a bottom of the tibial insert 2 to fit into a circumferential groove 13 defined in a tibial baseplate 1, thereby offering the efficacies of stable coupling, resistance against external forces, prevention of deformation and extension of lifespan and thus enhancing practicability and inventiveness of the present invention. The reinforcement 3 is directly set inside the through region 24 of the tibial insert 2, and a sleeve 31 of the reinforcement 3 has a circumferential outer surface 314 that forms threading or is made roughened, thereby providing the efficacies of increasing operation efficiency, providing safety of use, and making a stable coupling and thus enhancing the inventiveness and safety of the present invention. The components of the present invention are of modular designs and suit for difference of individuals and allow for partial replacement to thereby offer the efficacies of being easy to use and reducing costs and thus enhancing the practicability and convenience of the present invention. To conclude, the orthopaedic implant in accordance with the present invention provides excellent practicability, inventiveness, safety, and convenience.

Although the present invention has been described with reference to the preferred embodiment thereof, it is apparent to those skilled in the art that a variety of modifications and changes may be made without departing from the scope of the present invention which is intended to be defined by the appended claims.

What is claimed is:

1. An structural improvement of an orthopaedic implant of an artificial knee joint, comprising:
    a stem implantable into a proximal tibia, wherein an end of the stem has a coupling hole with an inner thread;
    a tibial baseplate, in which is formed a recess having a bottom that has a central portion defining a through hole extending through the tibial baseplate, and the end of the stem is inserted in the through hole, and the through hole has a top circumference that defines a circumferential groove extending outward, the recess has a side wall defining a retention slot;
    a tibial insert including a support and a projection, wherein an end of the tibial insert forms the projection, which corresponds; to the recess of the tibial baseplate and for press-fitting to the tibial baseplate, a retention pawl is formed on one side of the projection and is engageable with the retention slot of the tibial baseplate, and wherein the support is formed on an opposite end of the tibial insert, and a through region, formed in the support, extends through the tibial insert, wherein the through region includes a bore and an accommodating hole, wherein the accommodating hole is disposed in communication with; the bore, and the diameter of the accommodating hole is greater than the diameter of the bore, and the tibial insert forms two curved surfaces on opposite sides of the support to support contact and rolling; and
    a reinforcement fitted in the accommodating hole and comprising a sleeve and a bolt, wherein a first end of the sleeve forms a first opening, and a second end of the sleeve forms a stop with a second opening, wherein the first opening communicates with the second opening, and the bolt is movably; received in the sleeve, wherein the bolt comprises a bolt head and a bolt body, and the diameter of the bolt head is greater than the diameter of the second opening and the diameter of the bore, and the diameter of the bolt body is smaller than the diameter of the second opening, and the bolt body is in threading engagement with the inner thread of the coupling hole of the stem to drive the sleeve of the reinforcement to project beyond an end of the tibial insert for fitting into the groove of the tibial baseplate.

2. The structure improvement of the orthopaedic implant of the artificial knee joint as claimed in claim 1, wherein the sleeve of the reinforcement has an outer circumferential surface that forms a thread or is made roughened to improve tight engagement between the sleeve and the tibial insert.

* * * * *